United States Patent [19]

Bolhaar

[11] Patent Number: 5,369,482
[45] Date of Patent: Nov. 29, 1994

[54] METHOD AND APPARATUS FOR MEASURING THE REFRACTIVE INDEX OF INDEX MATCHING GELS AND LIKE SUBSTANCES

[75] Inventor: Antonius B. G. Bolhaar, Wadenoyen, Netherlands

[73] Assignee: The Whitaker Corporation, Wilmington, Del.

[21] Appl. No.: 936,172

[22] Filed: Aug. 27, 1992

[30] Foreign Application Priority Data

Aug. 29, 1991 [GB] United Kingdom ............... 9118524.9

[51] Int. Cl.$^5$ ............................................. G01N 21/41
[52] U.S. Cl. ....................................... 356/128; 356/133
[58] Field of Search ................................. 356/128, 133

[56] References Cited

U.S. PATENT DOCUMENTS 2,569,127  9/1951  Eltenton ............................ 356/133
4,907,878  3/1990  Arditty et al. ..................... 356/133

FOREIGN PATENT DOCUMENTS 491235   6/1992  European Pat. Off. ............ 356/128
3302089  7/1984  Germany ............................ 356/128
3408417 12/1984  Germany ............................ 356/128
138237   6/1988  Japan ................................. 356/133
2206201 12/1988  United Kingdom ................ 356/133

Primary Examiner—F. L. Evans
Attorney, Agent, or Firm—Adrian J. LaRue; Driscoll A. Nina

[57] ABSTRACT

An apparatus is disclosed for measuring the refractive index of index matching gels. A light source (10) is directed into one (20) of the output legs (20, 22) of an optical splitter (18), where the input leg (26) is interconnected to a fiber optic cable (27). The end of the cable (27) is inserted into the gel (30) to be measured. The incident light source (10) directs an incident light source through the splitter, and through the end (29) of the fiber optic cable (27). The difference in refractive indexes between the fiber optic cable (27) and the gel (30) causes a reflection of the incident light back to the splitter (18) and through a measuring device (52). By measuring the reflected power, and by knowing the incident power and other known factors, the refractive index of the gel can be calculated.

15 Claims, 4 Drawing Sheets

METHOD AND APPARATUS FOR MEASURING THE REFRACTIVE INDEX OF INDEX MATCHING GELS AND LIKE SUBSTANCES

BACKGROUND OF THE INVENTION

1. Field of the Invention

The subject invention relates to an apparatus for measuring the refractive index of index matching gels, and other substances having a variable refractive index.

2. BRIEF DESCRIPTION OF THE PRIOR ART

In the field of fiber optic devices where fiber cables must be spliced, it is known to splice fiber ends by way of index matching gels having an index of refraction equal to the index of refraction of the fibers to be spliced. It is also known to insert index matching gels at ends of fiber optic connectors to minimize losses at the interface of the connectors. Such an interconnection then is dependent on the accuracy to which the gel is matched to the fiber. If the gel does not match the fibers to be spliced, the interface between the two fibers will have losses associated thereat, due to the reflection caused by the difference in refractive index between the fiber and gel. Such losses could be detrimental to the electronic system for which the fibers are used.

Devices are known to measure the refractive index of index matching gels, one such device being known as the Abbe refractometer. One of the drawbacks to the Abbe refractometer is that the Abbe device can only give digital read outs, and cannot give measurements for varieties of temperatures, due to the method of making the measurements, as disclosed above.

Another disadvantage is that the Abbe refractometer cannot detect the extent to which the gel is mixed. Index matching gels are comprised of an oil and glass filler particles suspended in the oil. The glass filler particles should be selected such that the refractive index of the particles at all temperatures is the same as the refractive index of the fiber. The glass filler particles should also be thoroughly mixed in the oil to make a homogeneous gel. If the particles are not thoroughly mixed and clustered together, there will be light scattering, leading to power losses. As mentioned above, the Abbe refractometer cannot detect the extent to which the gel is mixed, but rather can give only an instantaneous value of the index of refraction for a given sample. A different sample, taken from another location may well have a different index of refraction. The index of refraction may also be time variable as the glass particles, if not properly mixed, tend to spin or rotate in the oil, and the index of refraction can change as the collected glass particles rotate.

Another disadvantage is that the Abbe refractometer measures the refractive index in the visible range. As the refractive index of matching gels is wavelength dependent, it would be advantageous to measure the refractive index of the gels at the wavelengths which are to be used, i.e. 1300 and 1500 nm. The invention explained herein measures the refractive index at such wavelengths.

SUMMARY OF THE INVENTION

An object of the invention then is to provide an apparatus for measuring the refractive index of index matching gels.

A further object of the invention is to provide an apparatus for measuring the refractive index of index matching gels, where the refractive index can be measured and plotted for a variety of temperatures.

Another object of the invention is to provide an apparatus for detecting whether the index matching gel is properly mixed.

The objects of the invention were accomplished by providing an apparatus for measuring the refractive index of a substance, where the apparatus comprises an optical splitter having an input interface, and first and second output interfaces. A light source is provided for emitting a light beam in a first direction, the light source being optically connected to the first output interface. Means are provided to optically connect the input interface of the optical splitter to the substance to be measured, the light beam being reflected back through the optical connection means, due to the refractive mismatch between the substance and optical connection means. Power detection means are optically connected to the second output interface to measure the output light power of the reflected light. In this manner, the refractive index of the substance is proportional to the reflected signal.

An inventive method of carrying out the objects of the invention comprise the steps of providing an incident light source to the mixture;

reflecting a portion of said light source back from the mixture, where the reflected light portion is dependent upon the refractive index of the mixture;

converting said reflected light portion into an electronic signal; and monitoring said electronic signal.

DETAILED DESCRIPTION OF THE PREFERRED EMBODIMENT

Figure 1:
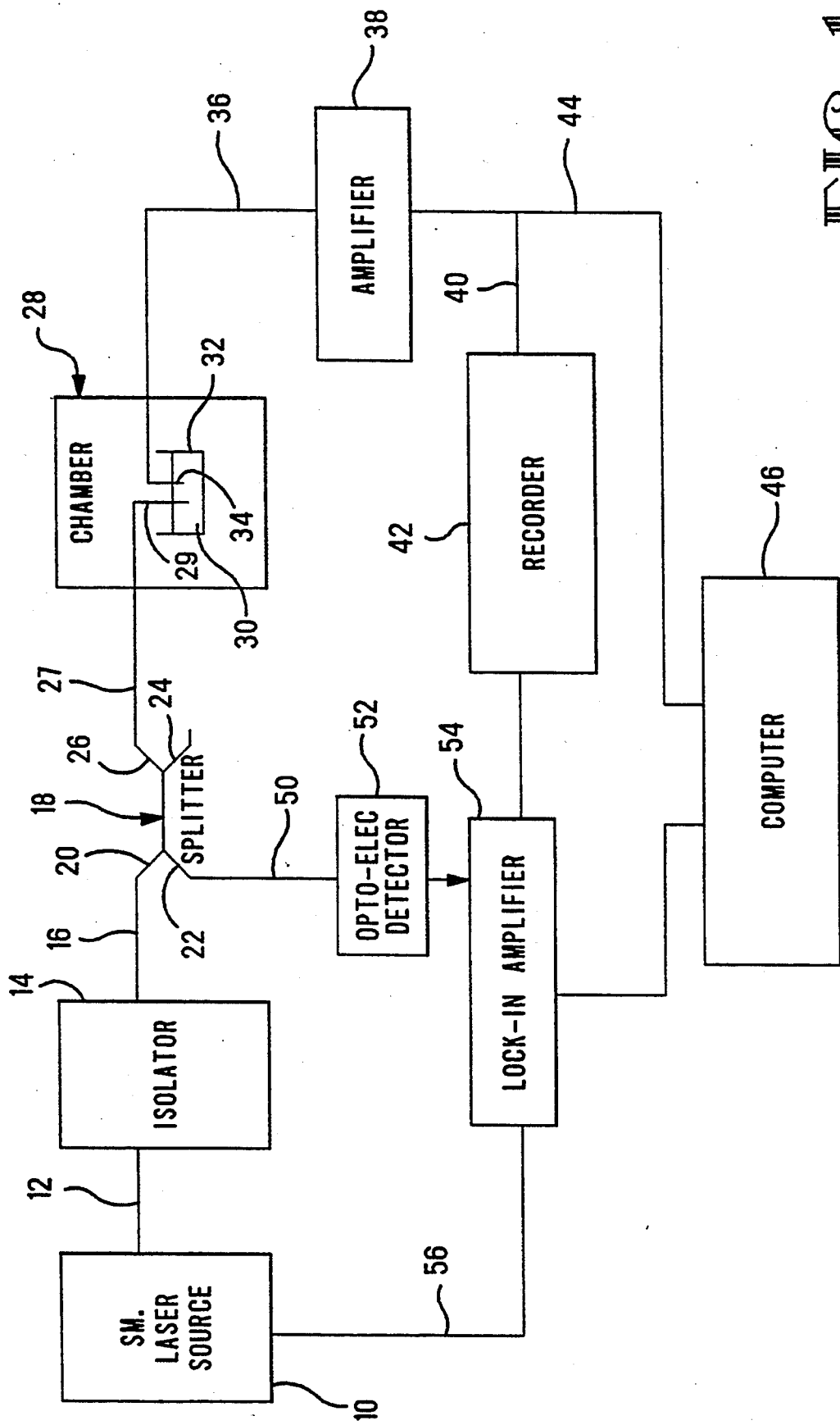
FIG. 1 is a schematic view of the apparatus of the present invention.

With reference now to FIG. 1, the mechanism for measuring the refractive index of substances is shown in schematic form. In the preferred embodiment of the invention, the device is used for measuring the refractive index of index matching gels of the typed used for splicing fiber optic cables. For example, the gel could be used in a splicing device, such as that shown in EP Publication 347,118. Advantageously, the device can also be used for matching the gels to particular fibers to achieve the maximum optical match between the fiber and gel.

With reference still to FIG. 1, the device is shown schematically as including a single mode laser source 10 having an incident power output at 12 which is directed through an optical isolator 14. The incident power output is directed through the optical isolator 14 at 16, and thereafter directed into an optical splitter 18. The splitter is a Y-type splitter having output branches 20 and 22, where in the preferred embodiment, the splitting ratio is 50–50 through each branch. In the preferred embodiment of the invention, the splitter 18 is a 2×2 splitter with the leg 24 fused into a ball to make the leg reflectionless.

It should be noted that the incident power output of the laser 10 is directed into the output side of the optical splitter 18 into output leg 20, whereas the input branch 26 of the optical splitter 18 is directed into a temperature control chamber 28. A light measuring device 27, in the form of a fiber optic cable, is inserted into the gel 30 to be measured, stored in a container, such as 32. As the chamber 28 is temperature controlled, a temperature monitoring device 34, such as a thermocouple, is also inserted in the sample 30. The output 36 of the thermocouple 34 is amplified at 38, and the temperature is recorded at 42. The amplified temperature signal is also directed at 44 to a computer at 46, which will be described in greater detail herein.

With reference still to FIG. 1, the output branch 22 of the optical coupler 18 is interconnected at 50 to a detector 52, which reads the optical output signal, and transforms it into an electronic signal, thereafter amplified through a lock-in amplifier at 54, and also directed to the computer 46. In the preferred embodiment of the invention, the detector 52 is a germanium power meter. It should also be noted that a reference signal 56 is directed from the laser 10 directly into the lock-in amplifier at 54. With the physical description of the system described as mentioned above, the operation will now be described in relation to FIG. 1.

A gel 30, to be measured, is inserted in the container 32 and placed in the chamber 28, at a prescribed temperature. The temperature is monitored as most gels are temperature-sensitive, being slightly negative, in the range of $-0.00030°$ to $-0.00040/°$ C. The single mode laser is thereafter excited causing an incident power beam at 12, which is directed through the optical isolator 14. The incident signal from the optical isolator 14 is thereafter directed into the output branch 20 of the optical coupler 18, and the beam is directed through the input branch 26 of the optical coupler 18, and through the fiber cable 27, used as the light medium. An end 29 of the fiber optic cable 27 is inserted into the gel 30 to be measured. As the index of refraction of the fiber 27 is different than the index of refraction of the gel, a reflection of the light is caused back through the fiber optic cable 27, towards the optic coupler 18. As the optical coupler has two output branches 20 and 22, the reflected signal will be subdivided into two signals, one through output branch 20 and one through output branch 22. The optical isolator 14 prevents back reflection of the reflected signal through output branch 20 of the optical coupler 18, thereby maintaining the stability of the laser output. Therefore, the portion of the reflected signal back through the output branch 20 is dissipated by the optical isolator 14.

The value of the reflected light, through the output branch 22, is dependent on the index of refraction of the gel, as shown below, where:

$$P_r = R \times P_{inc.} \times S$$

When:
$P_r$ = reflected power
$R$ = reflection coefficient
$P_{inc.}$ = incident power
$S$ = splitting ratio of optical coupler From the above formula, the refractive index of the gel to be measured can be calculated from the apparatus disclosed in FIG. 1, as follows.

The reflected power ($P_r$) is the value of the light power directed through fiber optic cable 50, and is measured by the detector 52. $P_{inc.}$ is known, as this is the incident light power from the laser source 10. S is also known, as this is the splitting ratio of the optical coupler 18, and in general, the splitting ratio is 50%, meaning that 50% of the reflected light will pass through branch 20 of the coupler, and 50% of the reflected light will pass through branch 22.

The reflection coefficient R, on the other hand, is not known, but the reflection coefficient is dependent on the index of refraction of the matching gel 30 and the index of refraction of the fiber, where:

$$R = \frac{n_c - n_s^2}{n_c + n_s}$$

where
$n_s$ = refractive index of sample gel
$n_c$ = refractive index of fiber cable As mentioned above, the apparatus includes a signal 56 positioned directly between the laser 10 and the lock-in amplifier 54. This signal 56 provides a reference from which the lock-in amplifier can measure. It should be appreciated that the reflected signal into the lock-in amplifier also contains spurious signals, such as directivity, Rayleigh scattering and various forms of noise. By providing a reference signal 56 directly into the lock-in amplifier 54, the lock-in amplifier can select only the value of the signal at the desired frequency range. For example, if the laser 10 operates at 1000 Hz, then the reference signal 56 to the lock-in amplifier will also be 1000 Hz, and the lock-in amplifier will select only that portion of the reflected signal operating at 1000 Hz.

When calculating the reflection coefficient, the directivity must be taken into account, such that:

$$R = \frac{P_r - P_{dir}}{P_{inc} \times S}$$

By equating the two formulas for the reflection coefficient, the refractive index of the sample can be calculated. Equating the two formulas for the reflection coefficient yields:

$$\frac{n_c - n_s^2}{n_c + n_s} = \frac{P_r - P_{dir}}{P_{inc} \times S}$$

Thus, by measuring the reflected power ($P_r$) at 52, the directivity ($P_{dir}$), and by knowing the refractive index ($n_c$) of the fiber cable 29, the index of refraction of the sample gel can be calculated.

In fact, the index of refraction for the entire temperature range can be calculated, by varying the temperature within the chamber 28. Advantageously, by having both the thermocouple 34 and reflection signal fed into the computer 46, the refractive index can be plotted versus temperature.

Alternatively, the index of refraction of the sample could be calculated by first taking a reference measurement in air, given that the index of refraction in air is 1.0. The reflection coefficient ($R_1$) in air is:

$$R_1 = \frac{n_c - n_o^2}{n_c + n_o}.$$

where:

$n_c$ = refractive index of the fiber core
$n_o$ = refractive index of air = 1.0.

Similarly, the reflection coefficient of the sample is:

$$R_s = \frac{n_c - n_s^2}{n_c + n_s}$$

where:

$n_s$ = refractive index of sample.

The relative reflection is the ratio between the reflection in air and of the sample which is:

$$R_{rel} = \frac{R_s}{R_1}$$

or $$\frac{\dfrac{n_c - n_s^2}{n_c + n_s}}{\dfrac{n_c - n_o^2}{n_c + n_o}} = \frac{\dfrac{P_s - P_{dir}}{P_{inci} \cdot S}}{\dfrac{P_1 - P_{dir}}{P_{inc \cdot s}}}$$

where the right half of the equation can be simplified to:

$$\frac{P_s - P_{dir}}{P_1 - P_{dir}}$$

Advantageously then, this particular method eliminates the need to measure the incident power, thereby minimizing the risk of saturating the detector. Furthermore, there is no need to measure and correct for the splitting ratio as that term cancels out also. The resulting equation is:

$$\frac{\dfrac{n_c - n_s^2}{n_c + n_s}}{\dfrac{n_c - n_o^2}{n_c + n_o}} = \frac{P_s - P_{dir}}{P_1 - P_{dir}}$$

The refractive index of the fiber core ($n_c$), the refractive index of air ($n_o$), the reflected power using the sample gel ($P_s$), the reflected power with the fiber core in air ($P_1$), and the directivity ($P_{dir}$) are either known or can be calculated, and therefore the refractive index of the gel sample ($n_s$) can be calculated.

In a situation where the refractive index of the fiber core ($n_c$) is not known, the index of the core can be calculated by using two reference fluids which have known indices of refraction ($n_1$, $n_2$). The reflection coefficient of the first reference fluid is:

$$R_r^1 = \frac{n_c - n_1^2}{n_c + n_1} = \frac{P_{r1} - P_{dir}}{P_{inci} \times S}$$

and the reflection coefficient of the second reference fluid is:

$$R_r^2 = \frac{n_c - n_2^2}{n_c + n_2} = \frac{P_{r2} - P_{dir}}{P_{inci} \times S}$$

From these two equations, the refractive index of the fiber core ($n_c$) can be calculated. If it is then necessary to calculate the refractive index of the sample, this can be done by following the approach in the previous method. For example, the refractive index of the sample can be calculated by knowing that the reflection coefficient is:

$$R_s = \frac{n_c - n_s^2}{n_c + n_s} = \frac{P_s - P_{dir}}{P_{inci} \times S}$$

and that the relative reflection is:

$$\frac{R_s}{R_{r1}} = \frac{\dfrac{n_c - n_s^2}{n_c + n_s}}{\dfrac{n_c - n_1^2}{n_c + n_1}} = \frac{P_s - P_{dir}}{P_{r1} - P_{dir}}$$

As with previous methods, the refractive index of the sample ($n_s$) can therefore be calculated.

Figure 2:
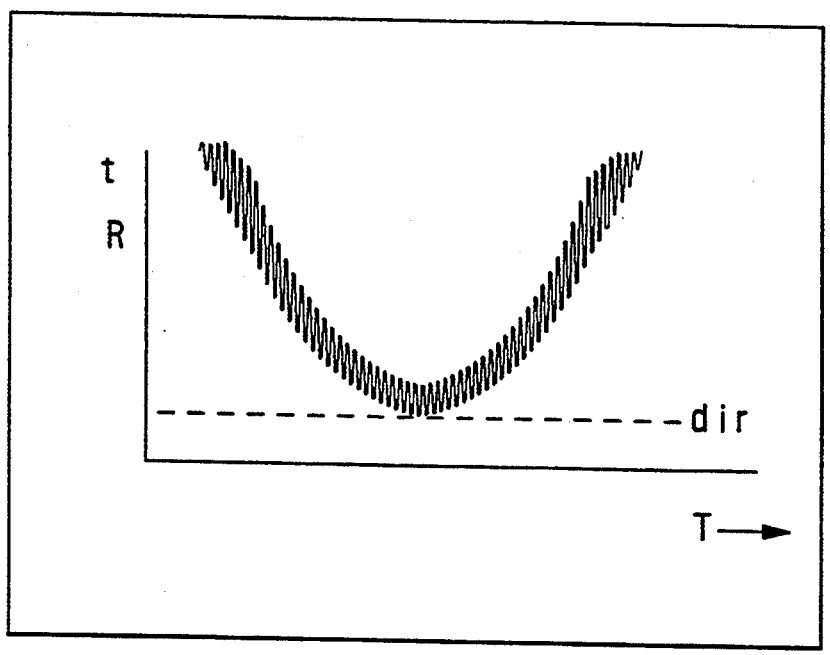
FIG. 2 shows a curve plotted by the present invention where noise is present.

It should also be appreciated that, unlike prior art refractometers, the present invention will plot the entire refractive index versus temperature curve on the X—Y recorder 42. As the matching gel is a combination of oil and glass particles, if the particles are not properly mixed, scattering noise will be present and will be plotted out on the X—Y recorder 42, in a plot similar to that shown in FIG. 2. If such a plot is present, the gel requires further mixing, as the improperly mixed gel will not have a uniform refractive index. Furthermore, the refractive index will be time dependent, as the unmixed glass particles tend to collect together, and the entire collection spins in the oil, producing a time variable refractive index. No prior art measuring devices can produce such a curve showing the scattering noise, but rather only shows a digital measurement of the refractive index.

Figure 3:
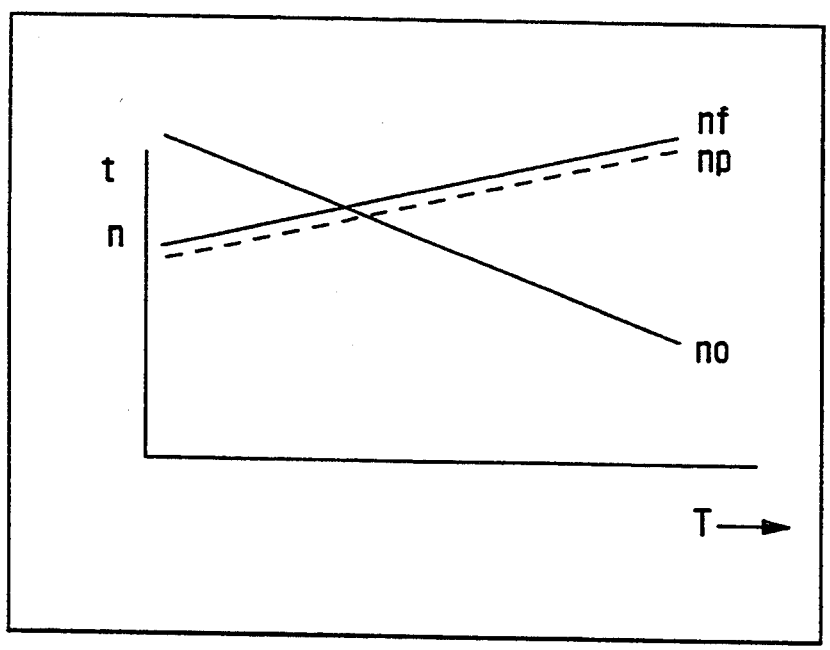
FIG. 3 is a curve representative of refractive index versus temperature of an ideal gel.
Figure 4:
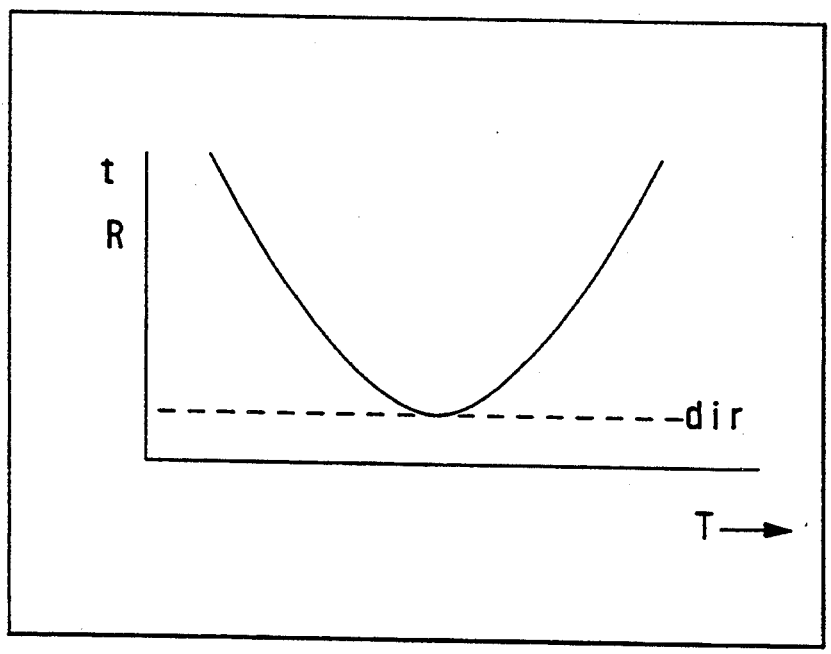
FIG. 4 is a curve representative of reflection versus temperature of an ideal gel.
Figure 5:
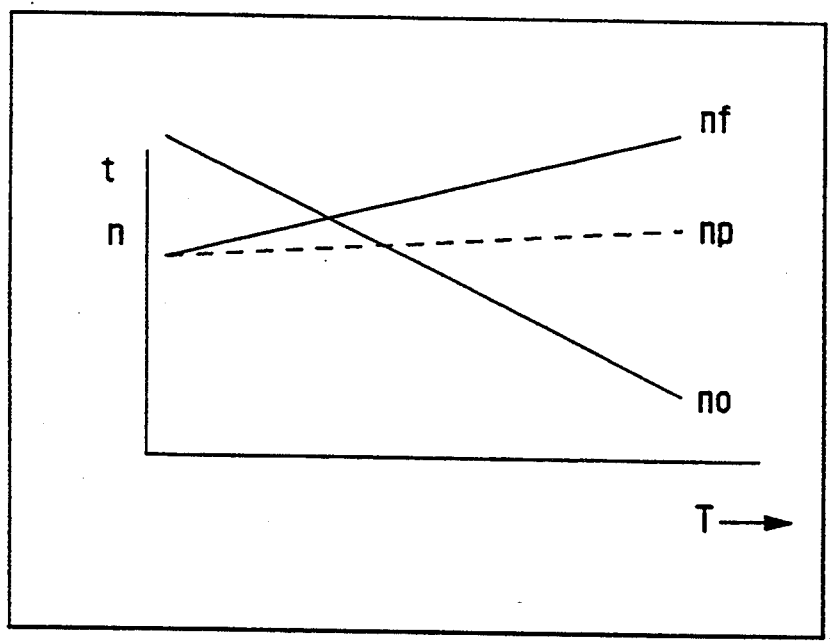
FIG. 5 is a curve representative of refractive index versus temperature of an improperly mixed gel.
Figure 6:
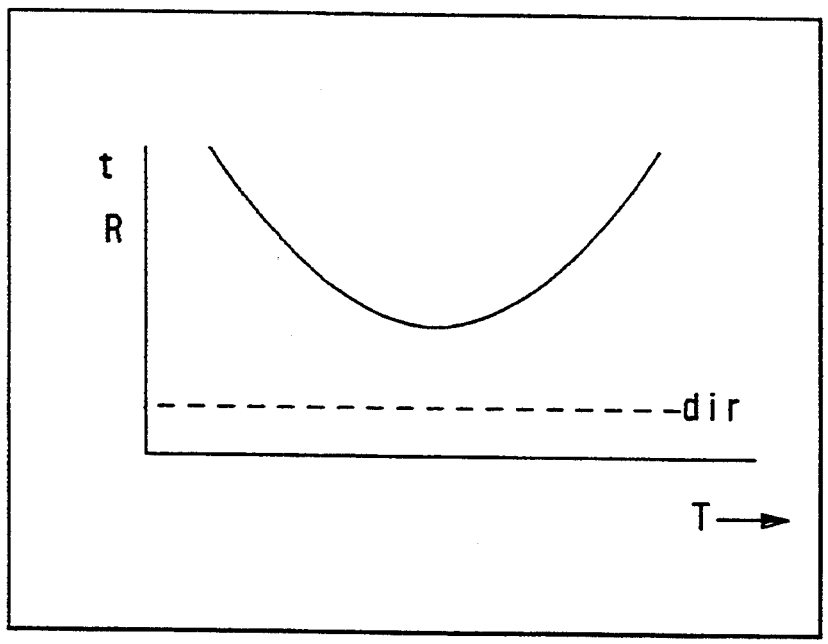
FIG. 6 is a curve representative of reflection versus temperature of an improperly mixed gel.

The apparatus is also useful for ensuring that the filler particles for the oil are properly selected, such that the refractive index of the filler particles are equal to the refractive index of the fiber to be spliced. When the index of refraction of the filler particles equals the index of refraction of the fiber, the curves for refractive index versus temperature, and reflection versus temperature would resemble FIGS. 3 and 4, respectively. If, however, the glass particles were chosen with an index of refraction unequal to the index of refraction of the fiber, the curves for refractive index versus temperature, and reflection versus temperature would resemble FIGS. 5 and 6, respectively. As shown in FIG. 5, the curve for the index of refraction of the particles is not collinear with the index of refraction of the fibers, which means that in the reflection curve of FIG. 6, the minimum measured signal is larger than the directivity of the splitter.

Advantageously, the above apparatus can also be used in dynamic systems where the index of refraction is dependent upon a mixture ratio of a solution. Such an apparatus could be used to monitor the mixture ratio. For example, in a system where sugar and water are mixed, the index of refraction is dependent upon the mixed ratio. Rather than having to take samples of the mixture and statically test the solution ratio, the mixture could be dynamically monitored by the above apparatus, and the mixing ratio adjusted accordingly.

While the form of apparatus herein described constitute a preferred embodiment of this invention, it is to be understood that the invention is not limited to this precise form of apparatus, and that changes may be made therein without departing from the scope of the invention which is defined in the appended claims.

What is claimed is:

1. An apparatus for measuring the refractive index of a subsance, the apparatus comprising:
    an optical splitter having an input interface, and first and second output interfaces;
    a light source for emitting a light beam in a first direction, said light source being optically connected to said first output interface;
    a fiber optic member optically connecting said input interface of said optical splitter to the substance to be measured, said fiber optic member having an end face adapted to cause a reflection of said light beam back through said fiber optic member due to the refractive mismatch between the substance and said fiber optic member; and
    a power detector optically connected to said second output interface to measure the output light power of the reflected light, whereby
    the refractive index of the substance is proportional to the reflected signal.

2. The apparatus of claim 1, wherein said light source is a single mode laser source.

3. The apparatus of claim 1, further comprising means to prevent back reflection into said light source.

4. The apparatus of claim 3, wherein said means to prevent back reflection comprises an optical isolator positioned medially between said light source and said optical splitter.

5. The apparatus of claim 1, wherein said optical splitter is a Y-type splitter, adapted for evenly splitting an incoming light source into two even split sources.

6. The apparatus of claim 1, further comprising a temperature controlled chamber for controlling the temperature of the substance to be measured, said fiber optic member being sealingly fed into said chamber.

7. The apparatus of claim 1, wherein said fiber optic member comprises a fiber optic cable for insertion into a sample of the substance.

8. The apparatus of claim 1, wherein the power detector converts said reflected optical signal to an electronic output signal.

9. The apparatus of claim 1, further comprising means to compute the refractive index of the substance from said reflected optical signal.

10. The apparatus of claim 9, further comprising means to detect the temperature of the substance, and feed back means electrically connected to said temperature detection means to feed back an electronic signal to the computational means, proportional to the temperature.

11. In a process where a fluid and at least one substance are mixed, where the light refractive index of the mixture of fluid and substance is dependent upon the quantity of the substance in the solution, a method of monitoring the quantity of the substance in the solution comprises the steps of:
    providing an incident light beam from a single mode light source to the mixture;
    reflecting a portion of said incident light beam from said single mode light source back from the mixture, where the reflected light portion is dependent upon the refractive index of the mixture;
    converting said reflected light portion into an electronic signal; and
    monitoring said electronic signal.

12. The method according to claim 11, wherein said incident light source is provided by a laser.

13. The method according to claim 11, wherein said reflected light portion is reflected through an optical splitter.

14. The method of claim 11, wherein the temperature of the mixture is monitored.

15. The method of claim 11, wherein said monitored electronic signal is used to control the quantity of the substance in the solution.

* * * * *